United States Patent [19]

Shirakawa et al.

[11] 4,377,407
[45] Mar. 22, 1983

[54] ISONICOTINANILIDE DERIVATIVES, PLANT GROWTH REGULATING COMPOSITIONS AND USE

[75] Inventors: Norio Shirakawa, Saitama; Hiromi Tomioka; Masuo Koizumi, both of Tokyo; Masaki Takeuchi, Ohmiya; Hiroshi Sugiyama, Tokyo; Masanori Okada, Niiza; Masahiro Yoshimoto, Tokyo; Yoshitaka Iwane, Yokohama; Yasushi Murakami, Tokyo, all of Japan

[73] Assignee: Chugai Seiyaku Kabushiki Kaisha, Tokyo, Japan

[21] Appl. No.: 306,582

[22] Filed: Sep. 28, 1981

[30] Foreign Application Priority Data

Sep. 30, 1980 [JP] Japan .................................. 55-135112
May 14, 1981 [JP] Japan .................................. 56-71424
Jul. 2, 1981 [JP] Japan .................................. 56-102257

[51] Int. Cl.³ .................... A01N 43/40; C07D 213/81
[52] U.S. Cl. ........................................... 71/76; 71/94; 546/323
[58] Field of Search ...................... 546/323; 71/76, 94

[56] References Cited

FOREIGN PATENT DOCUMENTS 53-72825 6/1978 Japan.
2047701 12/1980 United Kingdom.

OTHER PUBLICATIONS

"Chemical Abstracts" 90:1676.

Primary Examiner—Robert W. Ramsuer
Attorney, Agent, or Firm—Browdy & Neimark

[57] ABSTRACT

Isonicotinanilide derivatives of the formula

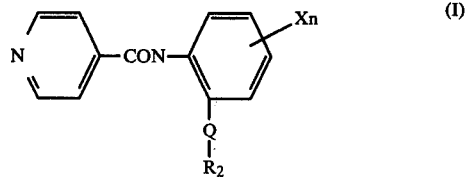

(wherein $R_1$ is a hydrogen atom or a lower alkyl group; X is a halogen atom or methyl; n is an integer of from 0 to 2; $R_2$ is phenyl, halo-substituted phenyl or a lower alkyl group; and Q is

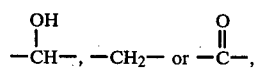

provided that Q is

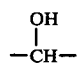

or $-CH_2-$ when $R_2$ is phenyl or halo-substituted phenyl, and Q is

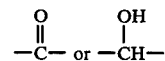

when $R_2$ is a lower alkyl group) a process for preparing the same and a plant growth regulator containing the same are disclosed. The derivatives of the formula above have good activity for regulating the growth of various plants, especially of grassy plants.

9 Claims, No Drawings

ISONICOTINANILIDE DERIVATIVES, PLANT GROWTH REGULATING COMPOSITIONS AND USE

This invention relates to isonicotinanilide derivatives of the formula (I):

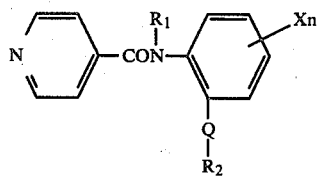

(wherein $R_1$ is a hydrogen atom or a lower alkyl group usually $C_1$-$C_4$ alkyl, preferably $C_1$-$C_2$ alkyl; X is a halogen atom such as F, Cl, Br or I, preferably Cl or Br, or methyl; n is an integer of from 0 to 2; $R_2$ is phenyl, halo-substituted phenyl such as mono- or di-fluoro, chloro, bromo- or iodo-substituted phenyl, preferably 2-chloro or 4-chloro phenyl, or a lower alkyl group usually $C_1$-$C_4$ alkyl; and Q is

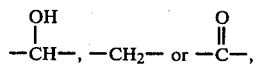

provided that when $R_2$ is phenyl or halo-substituted phenyl, Q is

or —CH$_2$—, and when $R_2$ is a lower alkyl group, Q is

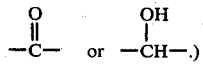

This invention also relates to a process for preparing the isonicotinanilide derivatives and to a plant growth regulator which contains one or more isonicotinanilide derivatives. The derivatives of the formula (I) have activity for regulating the growth of various plants, especially of grassy plants.

The biggest change in rice culture in recent years has been the remarkable development in mechanization of rice-trans planting and rice-harvesting. Thus, attention is being paid to development of seedlings tough enough to withstand mechanized transplantation and of culture technique for inhibiting falldown of rice plant during harvesting. For example, specific strains of rice such as Koshihikari, Sasanishiki and so on have become famous and are appreciated for their excellent taste. However, these strains of rice have some poor characteristics such as very low resistance to falldown and to pests. For these reasons, it has long been desired to establish good cultivation technique or to develop plant growth regulation with use of chemicals so that sufficiently tough seedlings and plants having good properties for mechanized harvesting can be realized.

The inventors of this invention have searched for several years to find compounds capable of regulating the growth of various plants, and found that isonicotinanilides represented by the formula (I) have excellent growth regulating activity, particularly with respect to grassy plants. On the basis of this fact, they have continued their study to complete this invention.

The compounds of this invention can be advantageously applied to inhibit useless unproductive growth, and excess aging in a rice seedling bed and to inhibit falldown in paddy field. In addition to these advantages, the compounds contribute to increase in the yield of rice. Also, these advantages are observed with respect to other grassy plants such as wheat, barley, corn, sugar cane or the like. Furthermore, the compounds of this invention exhibit an activity to inhibit undesirable growth of hypocotyl of broad-leaf plants, such as egg plant, cucumber and the like.

In addition to the crops above, the compounds are advantageously applied to lawn. Lawn is widely used in private and public gardens, golf links, green zones or greenbelts, the edge of roads, and the like. However, lawn is troublesome and costly to take care of; this is especially true in the summer when mowing must be done frequently because of rapid growth of the lawn and, therefore, is very expensive.

Also, various grassy plants other than lawn are planted on the edge or shoulder of roads or highway, greenbelts, highway or railroad banks, or the like. Taking care of these plants is not only costly and laborious, but also is very dangerous. Thus, the application of the compounds of this invention to these plants is very advantageous.

The compounds of the formula (I) can be used to regulate the growth of both broadleaf and grassy plants, and as a result of the regulation of growth, an improvement in resistance to poor growing circumstances and various pests can be expected.

Furthermore, the application of the compounds to crops increases the amount of chlorophyll in leaves to accelerate the photosynthesis activity and to promote the production of carbohydrate and the growth of roots.

A great advantage of this invention is that the compounds of this invention regulate the growth of plants, particularly the height of plants, and thicken the foliage and aid healthy growth without causing phytotoxicity such as leaf burn or foliage burn whatever type of treatment such as seed treatment, soil treatment or foliage treatment is selected.

The compounds of the formula (I) are novel and are prepared, for example, by the following process.

That is, the process comprises reacting an isonicotinyl halide of the formula (II)

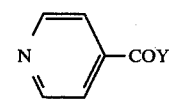

(wherein Y is a halogen atom) in a suitable solvent with an aniline derivative of the formula (III)

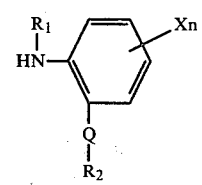

(wherein $R_1$, $R_2$, X, n and Q are the same as those defined above) to form the compound of the formula (I).

This reaction can be promoted by use of an acid removing agent, such as pyridine, triethylamine, sodium hydroxide, potassium hydroxide, sodium carbonate, potassium carbonate or the like.

A solvent useful in this reaction includes benzene, toluene, xylene, dichloromethane, chloroform, tetrahydrofuran, dioxane, dimethylformamide and the like. The reaction is carried out at room temperature but may be conducted at an elevated temperature or at a lower temperature depending on other reaction factors. The reaction temperature is preferably from 0° to 60° C. The reaction period varies depending on other specific reaction conditions, but usually ranges from 1 to 8 hours. After completion of the reaction, the product may be isolated and purified in a conventional way.

Alternatively, the compound of the formula (V)

$$\text{(V)}$$

(wherein $R_1$ is a hydrogen atom or a lower alkyl group; X is a halogen atom or methyl; n is an integer of from 0 to 2; $R_2$ is phenyl, halo-substituted phenyl or a lower alkyl; and Z is $$\begin{array}{c} \text{OH} \\ | \\ -\text{CH}- \end{array}$$

or —$CH_2$—, provided that Z is $$\begin{array}{c} \text{OH} \\ | \\ -\text{CH}- \end{array}$$

when $R_2$ is a lower alkyl group) can be prepared by reducing an isonicotinic acid derivative of the formula (IV)

$$\text{(IV)}$$

wherein $R_1$, $R_2$, X, and n are the same as those defined above with use of a reducing agent.

The reducing agent which is useful in this reaction includes metal hydrides such as aluminum lithium hydride, sodium borohydride and the like. The reaction with use of the reducing agent can be conducted in a conventional way.

Preparation of the compounds of this invention is further illustrated by the following exemplified preparation.

PREPARATION 1

N-Methyl-isonicotin-[4-chloro-2-(α-hydroxybenzyl)]anilide (Compound No. 3)

Isonicotinyl chloride hydrochloride (1.4 g) was added slowly over about 30 min. to a solution of 2-methylamino-5-chlorobenzhydrol (1.5 g) in pyridine (30 ml) while stirring under cooling with ice. After continuing the stirring at room temperature for 3 hours, water (200 ml) was added to the reaction mixture to precipitate crystals. The crystals were collected and recrystallized from methanol-acetone to give 1.7 g of N-methyl-isonicotin-[4-chloro-2-(α-hydroxybenzyl)]anilide having a melting point of 199°–201° C.

Analysis: Calcd. for $C_{20}H_{17}ClN_2O_2$ (molecular weight: 351.81): C, 68.08; H, 4.86; N, 7.04 (%). Found: C, 67.96; H, 4.98; N, 7.79 (%).

PREPARATION 2

Isonicotin-[4-chloro-2-(α-hydroxybenzyl)]anilide (Compound No. 4)

Sodium borohydride (0.2 g) was added slowly over about 30 min. to a solution of isonicotin-(4-chloro-2-benzoyl)anilide (1.9 g) in methanol (20 ml). After continuing the stirring at room temperature for 2 hours, water (200 ml) was added to the reaction mixture to precipitate crystals. The crystals were collected by filtration and recrystallized from dimethylformamide-methanol to give 1.8 g of isonicotin-[4-chloro-2-(α-hydroxybenzyl)]anilide having a melting point of 210°–212° C.

Analysis: Calcd. for $C_{19}H_{15}ClN_2O_2$ (molecular weight: 338.79): C, 67.36; H, 4.46; N, 8.27 (%). Found: C, 67.18; H, 4.56; N, 8.29 (%).

PREPARATION 3

Isonicotin-(4-chloro-2-benzyl)anilide (Compound No. 1)

Isonicotinyl chloride hydrochloride (1.4 g) was added slowly over about 30 min. to a solution of 4-chloro-2-benzylaniline (1.3 g) in pyridine (30 ml) while stirring under cooling with ice, followed by stirring at room temperature for 3 hours to complete the reaction. Water (200 ml) was added to the reaction mixture to precipitate crystals which were collected. Recrystallization of the crystals from ethanol gave 1.6 g of isonicotin-(4-chloro-2-benzyl)anilide having a melting point of 178°–179° C.

Analysis: Calcd. for $C_{19}H_{15}ClN_2O$ (molecular weight: 322.79): C, 70.70; H, 4.68; N, 8.68 (%). Found: C, 70.75; H, 4.79; N, 8.65 (%).

PREPARATION 4

Isonicotin-2-acetylanilide (Compound No. 18)

Isonicotinyl chloride hydrochloride (2.14 g) was added slowly to a solution of 2-aminoacetophenone (1.35 g) in pyridine (30 ml) while stirring under cooling with ice, followed by stirring at room temperature for 8 hours. Water was then added to the reaction mixture to precipitate crystals which were recovered by filtration and recrystallized from n-hexaneethylacetate to give 2.23 g of isonicotin-2-acetylanilide having a melting point of 116°–117° C. (Yield: 93%).

Analysis: Calcd. for $C_{14}H_{12}N_2O_2$ (molecular weight: 240.26): C, 69.99; H, 5.03; N, 11.66 (%). Found: C, 70.08; H, 4.98; N, 11.60 (%).

PREPARATION 5

Isonicotin-2-acetyl-4-chloroanilide (Compound No. 19)

Preparation 1 was repeated, except that 2-amino-5-chloroacetophenone (1.7 g) was used instead of 2- aminoacetophenone to give 2.5 g of isonicotin-2-acetyl-4-chloroanilide having a melting point of 203°–205° C. (Yield: 90%).

Analysis: Calcd. for $C_{14}H_{11}ClN_2O_2$ (molecular weight: 274.71): C, 61.21; H, 4.04; N, 10.20 (%). Found: C, 61.09; H, 3.99; N, 10.24 (%).

PREPARATION 6

Isonicotin-4-chloro-2-(α-hydroxyethyl)anilide (Compound No. 20)

Sodium borohydride (0.34 g) was added slowly to a solution of isonicotin-2-acetyl-4-chloroanilide (2.5 g) prepared in Preparation 2 in methanol (30 ml) while stirring under cooling with water. After stirring at room temperature for 3 hours, the reaction mixture was evaporated under reduced pressure to remove methanol and then water (100 ml) was added to the residue to precipitate crystals. The crystals were recovered by filtration and recrystallized from n-hexane-ethyl acetate to give 2.3 g of isonicotin-4-chloro-2-(α-hydroxyethyl)anilide having a melting point of 142°–143° C. (Yield: 92%).

Analysis: Calcd. for $C_{14}H_{13}ClN_2O_2$ (molecular weight: 276.62): C, 60.77; H, 4.74; N, 10.12 (%). Found: C, 60.70; H, 4.77; N, 10.08 (%).

The following Table 1 shows exemplary compounds of the formula (I) which were prepared as in the Preparations above. These listed compounds are shown for illustrative purposes only and are by no means intended to limit the scope of the invention. The reference No. for defining these compounds will be used in Examples of formulation and Experiments hereunder.

TABLE 1

| Compound No. | Chemical Structure | m.p. (°C.) |
|---|---|---|
| 1 | | 178–179 |
| 2 | | 144–145 |
| 3 | | 199–201 |
| 4 | | 210–212 |
| 5 | 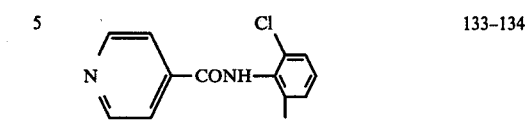 | 133–134 |
| 6 | 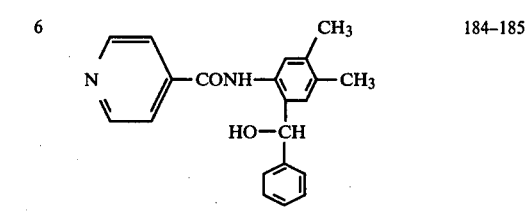 | 184–185 |
| 7 | 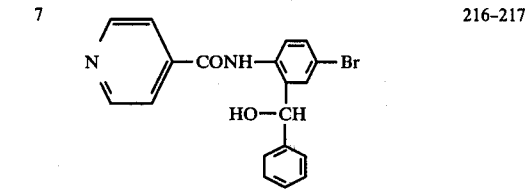 | 216–217 |
| 8 | 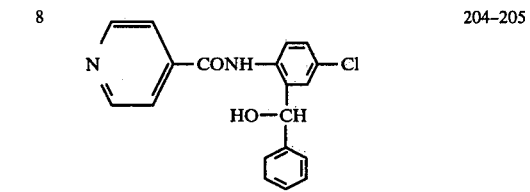 | 204–205 |
| 9 | 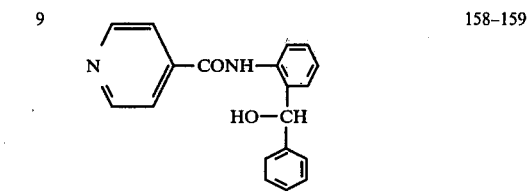 | 158–159 |
| 10 | 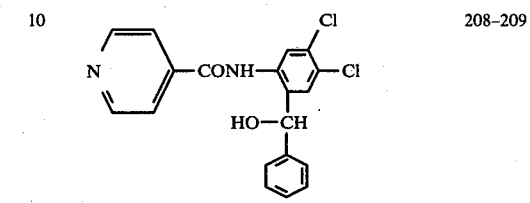 | 208–209 |
| 11 | 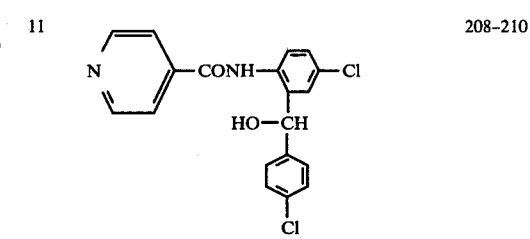 | 208–210 |

TABLE 1-continued

| Compound No. | Chemical Structure | m.p. (°C.) |
|---|---|---|
| 12 | Isonicotinamide N-ethyl, N-(2-(α-hydroxybenzyl)-4-chlorophenyl) | 206–207 |
| 13 | N-(2-benzylphenyl)isonicotinamide | 119.5–120.5 |
| 14 | N-(4-chloro-2-(4-chlorobenzyl)phenyl)isonicotinamide | 209–211 |
| 15 | N-(4-chloro-2-(2-chlorobenzyl)phenyl)isonicotinamide | 152–153 |
| 16 | N-(4-bromo-2-benzylphenyl)isonicotinamide | 177–177.5 |
| 17 | N-(2-(1-hydroxyethyl)phenyl)isonicotinamide | 123–124 |
| 18 | N-(2-acetylphenyl)isonicotinamide | 116–117 |
| 19 | N-(4-chloro-2-acetylphenyl)isonicotinamide | 203–205 |
| 20 | N-(4-chloro-2-(1-hydroxyethyl)phenyl)isonicotinamide | 142–143 |
| 21 | N-methyl-N-(2-(1-hydroxyethyl)phenyl)isonicotinamide | 143–144 |
| 22 | N-(2-propionylphenyl)isonicotinamide | 138–140 |
| 23 | N-(2-butyrylphenyl)isonicotinamide | 137–139 |
| 24 | N-(2-(1-hydroxypropyl)phenyl)isonicotinamide | 158–159 |
| 25 | N-(2-(1-hydroxybutyl)phenyl)isonicotinamide | 89–91 |
| 26 | N-(2-isobutyrylphenyl)isonicotinamide | 127–128 |
| 27 | N-(2-(1-hydroxy-2-methylpropyl)phenyl)isonicotinamide | 55–57 |
| 28 | N-methyl-N-(4-chloro-2-acetylphenyl)isonicotinamide | Oil NMR (CDCl$_3$)δ 2.35 (3H,S) 3.36 (3H,S) 7.09–7.60 (5H,m) 8.45–8.52 (2H,d) |

TABLE 1-continued

| Compound No. | Chemical Structure | m.p. (°C.) |
|---|---|---|
| 29 | 4-pyridyl-CON(CH$_3$)-C$_6$H$_3$(Cl)(CH(OH)CH$_3$) | 153–154 |
| 30 | 4-pyridyl-CONH-C$_6$H$_3$(Cl)(C(=O)C$_2$H$_5$) | 151–153 |
| 31 | 4-pyridyl-CONH-C$_6$H$_3$(Cl)(CH(OH)C$_2$H$_5$) | 133–134 |
| 32 | 4-pyridyl-CONH-C$_6$H$_3$(Cl)(C(=O)C$_3$H$_7$) | 131–132 |
| 33 | 4-pyridyl-CONH-C$_6$H$_3$(Cl)(CH(OH)C$_4$H$_7$) | 161–162 |
| 34 | 4-pyridyl-CONH-C$_6$H$_3$(Cl)(C(=O)CH(CH$_3$)$_2$) | 141–142 |
| 35 | 4-pyridyl-CONH-C$_6$H$_3$(Cl)(CH(OH)CH(CH$_3$)$_2$) | 142–143 |
| 36 | 4-pyridyl-CONH-C$_6$H$_3$(Br)(C(=O)CH$_3$) | 207–208 |
| 37 | 4-pyridyl-CONH-C$_6$H$_3$(Br)(CH(OH)CH$_3$) | 156–157 |

In accordance with this invention, the plant growth regulator is applied to plants in any suitable dose, usually in a dose such that a compound of the formula (I) or a mixture of two or more compounds of the formula (I) is 50–2,000 g/10 ares, preferably 200–1,000 g/10 ares, although the dose of the regulator may vary depend on the species and growth level of the plants to be regulated.

The compounds of this invention can be formulated in a conventional way using a solid or liquid carrier commonly used in the formulation of agricultural compositions into wettable powder, emulsion, dust, granules, tablet or the like. According to the necessity, a conventional adjuvant, such as dispersant, diluent, emulsifier, penetrating agent, binder or the like may be added. Further, a herbicidal compound, fungicidal compound, insecticidal compound, other plant growth regulator, fertilizer or the like may be incorporated into the formulation of this invention.

The activities of the plant growth regulator of this invention were confirmed by the following Experiments.

EXPERIMENT 1

Growth Regulating Test for Grassy Plants by Pre-emergence Soil Treatment

A pot with the open area of 1/5000 are was filed with dry clayish loam, seeded with bentgrass, Kentucky bluegrass, wild lawn, cucumber, green gram, komatsuna (*Brassica Rapa* Var. pervidis), nutsedge (*Cyprus microiri*), crabgrass, rice, or corn, and lightly covered with the same soil. The pot was sprayed with an aqueous dispersion of the wettable powder formulated in Example 1 in a dose of 250 g or 500 g of the active compound per 10 ares by using a portable sprayer. Fifty days after spraying, the height of the plant in connection with each pot was observed.

The results are shown in Table 2 below.

The degree of growth regulating activity for each plant was rated on the following scale.

0: 0–10% growth inhibition (in terms of untreated section)
1: 11–20% growth inhibition
2: 21–30% growth inhibition
3: 31–40% growth inhibition
4: 41–50% growth inhibition
5: more than 51% growth inhibition

TABLE 2

| Test Compound No. | Dose (g/10a) | Growth Regulating Activity | | | | | | | | | Injury |
|---|---|---|---|---|---|---|---|---|---|---|---|
| | | Bent-grass | Kentucky bluegrass | Cucumber | Green gram | Komatsuna | Nutsedge | Crab-grass | Rice plant | Corn | |
| 1 | 500 | 5 | 5 | 5 | 2 | 5 | 5 | 5 | 3 | 3 | none |
|   | 250 | 5 | 5 | 4 | 1 | 4 | 5 | 5 | 2 | 2 | " |
| 2 | 500 | 2 | 2 | 0 | 1 | 2 | 3 | 2 | 0 | 1 | " |
|   | 250 | 0 | 0 | 0 | 0 | 2 | 2 | 1 | 0 | 0 | " |
| 3 | 500 | 2 | 2 | 1 | 1 | 2 | 3 | 2 | 1 | 0 | " |
|   | 250 | 1 | 1 | 0 | 0 | 1 | 2 | 1 | 0 | 0 | " |
| 4 | 500 | 5 | 5 | 5 | 2 | 2 | 5 | 5 | 3 | 3 | " |
|   | 250 | 5 | 5 | 5 | 1 | 1 | 5 | 5 | 2 | 2 | " |
| 5 | 500 | 5 | 5 | 1 | 1 | 5 | 3 | 3 | 1 | 2 | " |
|   | 250 | 5 | 5 | 0 | 0 | 5 | 3 | 2 | 1 | 1 | " |
| 6 | 500 | 2 | 2 | 1 | 0 | 5 | 2 | 3 | 1 | 1 | " |
|   | 250 | 1 | 1 | 1 | 0 | 4 | 1 | 2 | 0 | 0 | " |
| 7 | 500 | 5 | 5 | 4 | 2 | 3 | 5 | 5 | 3 | 3 | " |
|   | 250 | 5 | 5 | 4 | 1 | 2 | 5 | 5 | 2 | 2 | " |
| 8 | 500 | 5 | 5 | 2 | 1 | 4 | 3 | 3 | 1 | 1 | " |
|   | 250 | 3 | 2 | 1 | 0 | 3 | 3 | 2 | 0 | 0 | " |
| Non-treated | — | 0 | 0 | 0 | 0 | 0 | 0 | 0 | 0 | 0 | — |

EXPERIMENT 2

Growth Regulating Test for Grassy Plants by Foliage Treatment

The compound of this invention formulated as in Example 2 was diluted with water and sprayed by a portable sprayer on the foliage of each of bentgrass, Kentucky bluegrass, cucumber, tomato and crabgrass which had been cultivated as in Experiment 1 to have a height of 5–6 cm. The dose of the sprayed active compound was 250 g of 500 g per 10 ares. Thirty days after spraying, the height of each plant was measured and averaged.

The results are shown in Table 3.

The rating of plant growth inhibition in Table 3 is the same as that illustrated in Experiment 1.

TABLE 3

| Test Compound No. | Dose (g/10a) | Growth Regulating Activity | | | | | Injury |
|---|---|---|---|---|---|---|---|
| | | Bent-grass | Kentucky bluegrass | Cucumber | Tomato | Crabgrass | |
| 1 | 500 | 5 | 5 | 3 | 2 | 5 | none |
|   | 250 | 5 | 5 | 2 | 1 | 5 | " |
| 2 | 500 | 4 | 4 | 1 | 1 | 2 | " |
|   | 250 | 2 | 2 | 0 | 0 | 1 | " |
| 3 | 500 | 5 | 4 | 2 | 2 | 5 | " |
|   | 250 | 4 | 4 | 1 | 1 | 4 | " |
| 4 | 500 | 5 | 5 | 3 | 3 | 5 | " |
|   | 250 | 5 | 5 | 2 | 2 | 5 | " |
| 5 | 500 | 3 | 4 | 2 | 2 | 4 | " |
|   | 250 | 2 | 2 | 1 | 1 | 3 | " |
| 7 | 500 | 5 | 5 | 2 | 2 | 5 | " |
|   | 250 | 5 | 5 | 2 | 1 | 5 | " |
| 8 | 500 | 3 | 3 | 1 | 1 | 3 | " |
|   | 250 | 2 | 1 | 0 | 0 | 2 | " |
| Non-treated | — | 0 | 0 | 0 | 0 | 0 | — |

EXPERIMENT 3

Field Test for Lawn Growth Regulation by Foliage Treatment

Lawn (bentgrass) which had been cultivated in a field for three years since transplantation was divided into sections of 1 m square, and mowed to a grass height of 1 cm in the seasons when the lawn grows fast. The compound of this invention formulated as in Example 1 and diluted with water was sprayed by a sprayer at a dose of 1 g, 2 g or 4 g per 1 m square in terms of the active compound.

Forty days after spraying, the lawn was mowed to a grass height of 1 cm, and the weight of mowed raw lawn in each section was measured.

The results are shown in Table 4 below.

TABLE 4

| Test Compound No. | Dose (g/m$^2$) | Average Height of Plant (cm) | Weight of mowed Grass (g/m$^2$) | Injury |
|---|---|---|---|---|
| 1 | 1 | 4.3 | 195 | none |
|   | 2 | 3.2 | 162 | " |
|   | 4 | 2.8 | 130 | " |
| 4 | 1 | 3.4 | 180 | " |
|   | 2 | 2.5 | 135 | " |
|   | 4 | 2.2 | 120 | " |
| Non-treated | — | 8.9 | 380 | — |

EXPERIMENT 4

Unproductive Growth Inhibiting Test for Rice Seedlings by Pre-emergence Soil Treatment A box with 60 cm length, 30 cm width and 3 cm depth was filled with 3.2 kg of clayish loam, seeded with 200 g of germinated grains of rice (Koshihikari strain), and lightly covered with 0.8 kg of soil. The test compound formulated as in Example 1 and diluted with water was sprayed by a portable sprayer on the soil in a dose of 0.1 g, 0.5 g, 1.0 g, or 2.0 g per box. Forty days after spraying, the weight of the rice seedlings, number of leaves, area and height of foliages, and length and weight of roots were measured. The test was carried out in a growth chamber in which the temperature was maintained in the range of from 25° to 30° C.

The results are shown in Table 5 below.

In Table 5, the figures shown are the average of 50 seedlings and the weight is on a dry basis.

TABLE 5

| Test Compound No. | Dose (g/box) | Height of plant (cm) | Root length (cm) | Number of leaves | Area of leaves (cm/plant) | Foliage weight (mg/plant) | Root weight (mg/plant) | Injury |
| --- | --- | --- | --- | --- | --- | --- | --- | --- |
| Non-treated | — | 34.5 | 8.3 | 5.1 | 7.2 | 20.6 | 8.2 | — |
| 1 | 2 | 18.3 | 8.5 | 6.2 | 6.8 | 21.5 | 8.1 | none |
|  | 1 | 18.5 | 10.2 | 6.2 | 7.2 | 26.3 | 12.5 | " |
|  | 0.5 | 20.5 | 11.1 | 6.3 | 7.8 | 26.5 | 16.3 | " |
|  | 0.1 | 32.2 | 9.5 | 6.1 | 8.2 | 25.2 | 17.5 | " |
| 2 | 2 | 20.3 | 8.5 | 5.4 | 7.5 | 26.3 | 9.2 | " |
|  | 1 | 26.5 | 9.3 | 6.2 | 7.7 | 30.2 | 10.3 | " |
|  | 0.5 | 30.2 | 10.6 | 6.2 | 8.4 | 30.4 | 21.5 | " |
|  | 0.1 | 35.5 | 13.5 | 6.0 | 7.2 | 30.7 | 20.2 | " |
| 4 | 2 | 16.3 | 8.0 | 6.3 | 7.0 | 21.2 | 8.5 | " |
|  | 1 | 18.5 | 8.5 | 6.7 | 7.5 | 22.6 | 9.7 | " |
|  | 0.5 | 18.2 | 8.4 | 6.5 | 7.6 | 27.7 | 12.5 | " |
|  | 0.1 | 20.7 | 12.2 | 5.8 | 7.6 | 29.5 | 16.3 | " |

EXPERIMENT 5

Rice seedlings (Koshihikari strain) which had been grown in a seedling box were transplanted in the paddy field which was divided into sections of 2.5 m×2 m. Five seedlings were transplanted at one spot with the spots in one row spaced 30 cm apart, the rows being 12 cm apart. Forty days after the transplantation, the test compound formulated as in Example 1 and diluted with water was sprayed by a portable sprayer on the soil in a dose of 200 g, 400 g, or 600 g per 10 ares. Twenty days after coming into ears, the number of stalks and ears per spot, the length between 1st and 5th nodes of stalks, and the weight of dry stalk from 4th to 5th node were measured.

The results are shown in Table 6.

In Table 6, the figures shown are the average of 50 spots of plants.

TABLE 6

| Test Compound No. | Dose (g/10a) | Number of stalks per spot | Ear length (cm) | Length between nodes (cm) | | | | | | Unit stalk weight between nodes (mg/cm) | |
| --- | --- | --- | --- | --- | --- | --- | --- | --- | --- | --- | --- |
|  |  |  |  | 1st | 2nd | 3rd | 4th | 5th | Total | 4th | 5th |
| Non-treated | — | 28 | 18.4 | 35.0 | 20.2 | 14.5 | 8.0 | 3.2 | 80.9 | 10.2 | 22.0 |
| 1 | 600 | 35 | 19.0 | 32.2 | 12.7 | 4.4 | 1.4 | 0.8 | 51.5 | 23.3 | 42.5 |
|  | 400 | 32 | 19.3 | 34.8 | 14.0 | 7.6 | 4.1 | 1.2 | 61.7 | 29.2 | 42.0 |
|  | 200 | 30 | 19.8 | 35.0 | 16.2 | 10.2 | 5.2 | 2.0 | 68.6 | 19.8 | 33.0 |
| 4 | 600 | 38 | 19.2 | 30.6 | 12.5 | 4.7 | 1.2 | 0.7 | 49.7 | 30.5 | 62.5 |
|  | 400 | 32 | 18.6 | 31.0 | 12.2 | 4.5 | 1.2 | 0.8 | 49.7 | 25.5 | 55.0 |
|  | 200 | 35 | 17.0 | 30.7 | 15.8 | 9.6 | 2.8 | 0.8 | 59.7 | 25.2 | 50.0 |
| 7 | 600 | 33 | 19.1 | 34.3 | 16.4 | 9.6 | 4.1 | 1.0 | 65.4 | 31.2 | 56.2 |
|  | 400 | 33 | 19.0 | 35.6 | 15.9 | 9.7 | 5.6 | 1.6 | 68.4 | 30.2 | 45.5 |
|  | 200 | 32 | 19.2 | 35.0 | 16.2 | 10.2 | 5.2 | 2.0 | 68.6 | 15.8 | 33.7 |

EXPERIMENT 6

Growth Regulating Test for Cucumber and Rice Plant at Early Growing Stage (Germination Test in Petri Dishes)

Filter paper was placed on the bottom of a petri dish 9 cm in diameter, and after pouring 15 ml of a 10 ppm test compound aqueous solution into the dish, 10 seeds of cucumber (Tokiwa strain) and 10 seeds of rice (Sasanishiki strain) were placed on the paper. Tests were conducted by 3 runs for each test compound in a growth chamber having its temperature maintained at 25° C. Seventeen days after the placement of seeds, length of hypocotyl and roots and dry weight of foliage and roots for cucumber and height of plant, length of the second leaf sheath and dry weight of foliage and roots for rice plant were measured.

The results are shown in Table 7 on cucumber, and Table 8 on rice plant.

Each numeral in Tables 7 and 8 represents an average of 30 plants.

TABLE 7

| Test Compound No. | Dose (ppm) | Hypocotyl length (cm/plant) | Root length (cm/plant) | Foliage weight (mg/plant) | Root weight (mg/plant) | Injury |
| --- | --- | --- | --- | --- | --- | --- |
| Non-treated | — | 4.5 | 9.5 | 14.2 | 3.2 | — |
| 2 | 10 | 0.9 | 15.9 | 15.6 | 4.8 | none |
| 4 | 10 | 0.8 | 14.4 | 15.0 | 4.6 | " |
| 7 | 10 | 1.0 | 16.4 | 15.8 | 5.1 | " |
| 8 | 10 | 0.6 | 14.3 | 15.0 | 5.7 | " |
| 9 | 10 | 0.7 | 16.2 | 17.6 | 5.0 | " |
| 10 | 10 | 0.7 | 12.9 | 16.6 | 4.2 | " |
| 11 | 10 | 1.0 | 14.3 | 17.3 | 4.5 | " |
| 12 | 10 | 0.8 | 18.3 | 14.5 | 5.4 | " |
| 13 | 10 | 1.0 | 15.2 | 14.9 | 4.0 | " |
| 14 | 10 | 2.0 | 13.4 | 15.2 | 5.1 | " |
| 15 | 10 | 1.9 | 14.0 | 14.5 | 5.1 | " |
| 16 | 10 | 1.0 | 13.8 | 15.8 | 4.9 | " |

TABLE 8

| Test Compound No. | Dose (ppm) | Height of plant (cm) | Length of second leaf seath (cm) | Foliage weight (mg/plant) | Root weight (mg/plant) | Injury |
| --- | --- | --- | --- | --- | --- | --- |
| Non-treated | — | 8.4 | 3.9 | 4.2 | 4.0 | — |
| 2 | 10 | 4.2 | 2.1 | 4.0 | 7.2 | none |
| 4 | 10 | 3.6 | 1.5 | 3.2 | 6.0 | " |
| 7 | 10 | 3.7 | 1.6 | 3.5 | 6.8 | " |
| 8 | 10 | 3.8 | 1.7 | 3.9 | 7.5 | " |

TABLE 8-continued

| Test Compound No. | Dose (ppm) | Height of plant (cm) | Length of second leaf seath (cm) | Foliage weight (mg/plant) | Root weight (mg/plant) | Injury |
|---|---|---|---|---|---|---|
| 9 | 10 | 3.3 | 1.6 | 4.1 | 7.5 | " |
| 10 | 10 | 3.8 | 1.7 | 4.2 | 6.2 | " |
| 11 | 10 | 4.0 | 2.0 | 3.8 | 6.8 | " |
| 12 | 10 | 3.7 | 1.5 | 4.0 | 6.5 | " |
| 13 | 10 | 4.0 | 1.8 | 4.1 | 5.1 | " |
| 14 | 10 | 4.1 | 2.1 | 4.2 | 5.3 | " |
| 15 | 10 | 4.8 | 2.0 | 4.3 | 5.8 | " |
| 16 | 10 | 3.8 | 2.0 | 3.4 | 6.9 | " |

EXPERIMENT 7

Unproductive Growth Inhibiting Test for Rice Seedling with use of Test Compound-premixed Soil Wettable powder (2 g or 1 g) formulated as in Example 1 for each test compound was thoroughly mixed with 4 kg of soil. A seedling cultivation box 60 cm long, 30 cm wide and 3 cm deep was filled with 3.2 kg of the treated soil, seeded with 200 g of germinated grains of rice (Koshihikari strain), watered and lightly covered with the remaining soil (0.8 kg). The box was placed and retained in a growth chamber having its temperature maintained at 30° C. Twenty-five days after seedling, the height of the plant, length of roots, number of leaves and weight each of foliage and roots were measured.

The results are shown in Table 9.

Each number in Table 9 is an average of 50 seedlings, and the weight is on a dry basis.

TABLE 9

| Test Compound No. | Dose (g/box) | Height of plant (cm) | Root length (cm/plant) | Number of leaves | Foliage weight (mg/plant) | Root weight (mg/plant) | Injury |
|---|---|---|---|---|---|---|---|
| Non-treated | — | 26.5 | 6.5 | 3.8 | 18.5 | 5.9 | — |
| 1 | 2 | 15.3 | 9.5 | 4.1 | 18.1 | 8.6 | none |
|   | 1 | 19.6 | 12.5 | 4.2 | 18.3 | 10.2 | " |
| 4 | 2 | 12.2 | 8.7 | 4.3 | 16.3 | 6.3 | " |
|   | 1 | 15.1 | 8.5 | 4.2 | 18.9 | 8.4 | " |
| 9 | 2 | 16.2 | 9.1 | 4.5 | 17.4 | 7.2 | " |
|   | 1 | 18.3 | 10.2 | 4.2 | 18.2 | 9.9 | " |
| 12 | 2 | 14.1 | 8.6 | 4.5 | 16.1 | 10.5 | " |
|   | 1 | 18.4 | 10.3 | 4.1 | 17.9 | 10.6 | " |
| 16 | 2 | 13.5 | 9.2 | 4.3 | 16.7 | 8.5 | " |
| 16 | 1 | 19.2 | 10.1 | 4.2 | 18.4 | 11.4 | " |

EXPERIMENT 8

Growth Regulating Test for Cucumber and Rice Plant at Early Growing Stage (Germination Test in Petri Dishes)

Filter paper was placed on the bottom of a petri dish 9 cm in diameter, and after pouring 15 ml of a 10 ppm test compound aqueous solution into the dish, 10 seeds of cucumber (Tokiwa strain) and 10 seeds of rice (Sasanishiki strain) were placed on the paper. Tests were conducted by 3 runs for each test compound in a growth chamber having its temperature and brightness maintained at 25° C. and at 500 lux. Seventeen days after the placement of seeds, length of hypocotyl and roots and dry weight of foliage and roots for cucumber, and height of plant, length of the second leaf sheath and dry weight of foliage and roots for rice plant were measured.

The results are shown in Table 10 on cucumber, and Table 11 on rice plant.

Each number in Tables 10 and 11 is an average of 30 plants.

TABLE 10

| Test Compound No. | Dose (ppm) | Hypocotyl length (cm) | Root length (cm) | Foliage weight (mg/plant) | Root weight (mg/plant) | Injury |
|---|---|---|---|---|---|---|
| Non-treated | — | 6.0 | 9.8 | 15.3 | 3.2 | — |
| 17 | 50 | 1.0 | 13.7 | 15.2 | 4.1 | none |
|   | 10 | 1.1 | 14.3 | 15.3 | 4.5 | " |
|   | 1 | 1.2 | 11.0 | 15.6 | 4.8 | " |
| 18 | 50 | 0.6 | 7.5 | 18.4 | 2.9 | " |
|   | 10 | 2.5 | 9.7 | 15.0 | 3.0 | " |
|   | 1 | 2.6 | 9.9 | 16.8 | 3.0 | " |
| 19 | 50 | 1.9 | 10.7 | 15.4 | 4.6 | " |
|   | 10 | 2.3 | 10.6 | 16.2 | 5.8 | " |
|   | 1 | 2.4 | 11.0 | 15.0 | 4.2 | " |
| 20 | 50 | 0.7 | 9.5 | 14.2 | 4.1 | " |
|   | 10 | 1.0 | 12.2 | 15.8 | 5.2 | " |
|   | 1 | 1.1 | 14.1 | 16.1 | 4.6 | " |
| 21 | 50 | 1.0 | 10.2 | 14.3 | 4.2 | " |
|   | 10 | 1.2 | 13.5 | 15.6 | 5.1 | " |
|   | 1 | 1.8 | 14.1 | 15.4 | 4.6 | " |

TABLE 11

| Test Compound No. | Dose (ppm) | Height of plant (cm) | Length of second leaf seath (cm) | Root length (cm) | Foliage weight (mg/plant) | Root weight (mg/plant) | Injury |
|---|---|---|---|---|---|---|---|
| Non-treated | — | 7.1 | 4.2 | 5.1 | 4.3 | 3.6 | — |
| 17 | 50 | 4.3 | 1.1 | 6.3 | 4.0 | 4.8 | none |
|   | 10 | 5.0 | 1.2 | 5.8 | 4.2 | 5.4 | " |
|   | 1 | 5.2 | 1.5 | 6.2 | 4.2 | 4.5 | " |
| 18 | 50 | 3.8 | 1.2 | 4.9 | 3.8 | 3.8 | " |
|   | 10 | 3.9 | 1.2 | 5.0 | 4.1 | 4.1 | " |
|   | 1 | 4.2 | 1.4 | 5.5 | 4.4 | 4.2 | " |
| 19 | 50 | 6.0 | 2.0 | 7.5 | 4.3 | 5.1 | " |
|   | 10 | 6.2 | 2.4 | 8.4 | 4.5 | 6.2 | " |
|   | 1 | 6.5 | 3.0 | 7.2 | 4.6 | 5.0 | " |
| 20 | 50 | 4.0 | 1.0 | 5.8 | 4.0 | 4.1 | " |
|   | 10 | 4.3 | 1.0 | 6.5 | 4.0 | 5.5 | " |
|   | 1 | 4.8 | 1.2 | 6.1 | 4.1 | 4.6 | " |
| 21 | 50 | 4.0 | 1.1 | 5.8 | 4.1 | 4.5 | " |
|   | 10 | 4.3 | 1.3 | 6.7 | 4.4 | 5.2 | " |
|   | 1 | 5.2 | 1.7 | 6.9 | 4.2 | 5.6 | " |

EXPERIMENT 9

Unproductive Growth Inhibiting Test for Rice Seedling with use of Test Compound-premixed Soil Wettable powder (2 g, 1 g or 0.5 g) formulated as in Example 1 for each test compound was thoroughly mixed with 4 kg of soil. A seedling cultivation box of perforated bottomed plastic 60 cm long, 30 cm wide and 3 cm deep was filled with 3.2 kg of the treated soil, seeded with 150 g of germinated grains of rice (Koshihikari strain), watered and lightly covered with the remaining soil (0.8 kg). The box was placed for 2 days in a growth chamber having its temperature maintained at 25°–30° C., so that the seeds were germinated. Then, the box was moved a filled plastic hothouse. Twenty-five days after seeding, the height of the plant, length of roots, number of leaves and weight each of foliage and roots were measured.

The results are shown in Table 12.

Each number in Table 12 is an average of 50 seedlings, and the weight is on a dry basis.

TABLE 12

| Test Compound No. | Dose (g/box) | Height of plant (cm) | Root length (cm) | Number of leaves | Foliage weight (mg/plant) | Root weight (mg/plant) | Injury |
|---|---|---|---|---|---|---|---|
| Non-treated | — | 22.3 | 7.2 | 3.7 | 22.6 | 8.3 | — |
| 17 | 2 | 7.5 | 8.3 | 4.5 | 19.5 | 10.2 | none |
|  | 1 | 7.6 | 8.9 | 4.7 | 20.7 | 10.9 | " |
|  | 0.5 | 9.9 | 9.2 | 4.0 | 23.1 | 11.5 | " |
| 18 | 2 | 13.5 | 8.1 | 4.0 | 22.2 | 9.5 | " |
|  | 1 | 16.2 | 8.8 | 3.9 | 22.8 | 9.7 | " |
|  | 0.5 | 16.5 | 8.1 | 3.7 | 23.4 | 9.4 | " |
| 19 | 2 | 10.2 | 9.2 | 4.2 | 22.0 | 9.5 | " |
|  | 1 | 11.1 | 10.5 | 4.5 | 22.8 | 10.7 | " |
|  | 0.5 | 15.7 | 8.1 | 4.0 | 22.8 | 11.1 | " |
| 20 | 2 | 7.4 | 10.3 | 4.4 | 20.7 | 10.7 | " |
|  | 1 | 7.8 | 12.5 | 4.4 | 21.6 | 11.5 | " |
|  | 0.5 | 10.2 | 13.2 | 4.2 | 23.1 | 10.8 | " |
| 21 | 2 | 13.0 | 8.7 | 4.6 | 20.5 | 10.3 | " |
|  | 1 | 14.2 | 9.2 | 4.2 | 22.8 | 12.5 | " |
|  | 0.5 | 15.5 | 10.5 | 4.0 | 22.6 | 11.8 | " |
| 22 | 2 | 13.6 | 8.0 | 4.0 | 22.0 | 9.3 | " |
|  | 1 | 16.1 | 8.6 | 3.8 | 22.9 | 9.5 | " |
|  | 0.5 | 16.5 | 8.1 | 3.5 | 23.5 | 9.6 | " |
| 23 | 2 | 12.4 | 7.6 | 4.3 | 21.7 | 9.4 | " |
|  | 1 | 13.4 | 8.9 | 4.6 | 20.5 | 10.3 | " |
|  | 0.5 | 14.3 | 8.3 | 4.2 | 22.5 | 10.2 | " |
| 24 | 2 | 7.5 | 10.2 | 4.4 | 20.7 | 10.5 | " |
|  | 1 | 8.0 | 12.3 | 4.3 | 21.4 | 11.5 | " |
|  | 0.5 | 11.2 | 13.1 | 4.0 | 23.0 | 10.6 | " |
| 25 | 2 | 13.2 | 8.0 | 4.0 | 22.1 | 9.3 | " |
|  | 1 | 16.0 | 8.6 | 3.7 | 22.6 | 9.5 | " |
|  | 0.5 | 16.3 | 8.0 | 3.5 | 22.8 | 9.2 | " |
| 26 | 2 | 13.5 | 8.3 | 3.8 | 22.0 | 9.1 | " |
|  | 1 | 16.1 | 8.6 | 3.7 | 22.6 | 9.6 | " |
|  | 0.5 | 16.4 | 8.0 | 3.6 | 23.2 | 9.4 | " |
| 27 | 2 | 12.4 | 7.9 | 4.2 | 21.6 | 9.5 | " |
|  | 1 | 13.0 | 8.7 | 4.3 | 20.7 | 10.4 | " |
|  | 0.5 | 14.1 | 8.0 | 4.0 | 22.3 | 10.0 | " |
| 28 | 2 | 13.5 | 8.1 | 3.9 | 22.0 | 9.6 | " |
|  | 1 | 16.0 | 8.6 | 3.7 | 22.7 | 8.8 | " |
|  | 0.5 | 16.5 | 8.0 | 3.5 | 23.4 | 9.5 | " |
| 29 | 2 | 12.2 | 7.7 | 4.3 | 21.6 | 9.2 | " |
|  | 1 | 12.1 | 8.6 | 4.5 | 20.7 | 10.3 | " |
|  | 0.5 | 14.2 | 8.3 | 4.3 | 22.8 | 10.1 | " |
| 30 | 2 | 13.4 | 8.2 | 4.1 | 22.2 | 9.6 | " |
|  | 1 | 16.2 | 8.9 | 4.0 | 22.7 | 9.7 | " |
|  | 0.5 | 16.4 | 8.2 | 3.7 | 23.2 | 9.3 | " |
| 31 | 2 | 7.2 | 10.1 | 4.3 | 20.8 | 10.9 | " |
|  | 1 | 7.8 | 12.6 | 4.4 | 22.0 | 11.5 | " |
|  | 0.5 | 10.1 | 13.1 | 4.1 | 23.0 | 10.7 | " |
| 32 | 2 | 14.0 | 7.9 | 3.7 | 21.8 | 9.5 | " |
|  | 1 | 16.0 | 8.5 | 3.6 | 22.5 | 9.6 | " |
|  | 0.5 | 16.3 | 8.2 | 3.4 | 22.9 | 9.2 | " |
| 33 | 2 | 12.1 | 7.7 | 3.8 | 21.2 | 9.2 | " |
|  | 1 | 13.2 | 8.5 | 4.1 | 20.5 | 10.1 | " |
|  | 0.5 | 14.2 | 7.9 | 3.7 | 22.0 | 9.8 | " |
| 34 | 2 | 13.2 | 7.8 | 3.9 | 21.2 | 9.2 | " |
|  | 1 | 16.1 | 8.5 | 3.6 | 21.8 | 9.3 | " |
|  | 0.5 | 16.3 | 7.9 | 3.4 | 22.4 | 9.1 | " |
| 35 | 2 | 7.6 | 10.2 | 4.4 | 20.2 | 10.7 | " |
|  | 1 | 7.9 | 12.1 | 4.5 | 21.1 | 11.4 | " |
|  | 0.5 | 10.1 | 13.2 | 4.0 | 22.7 | 10.6 | " |
| 36 | 2 | 7.2 | 9.3 | 4.2 | 22.0 | 10.6 | " |
|  | 1 | 7.6 | 10.7 | 4.6 | 22.7 | 10.9 | " |
|  | 0.5 | 10.0 | 8.3 | 4.0 | 22.6 | 11.2 | " |
| 37 | 2 | 7.3 | 10.2 | 4.3 | 20.5 | 10.5 | " |
|  | 1 | 7.8 | 12.3 | 4.5 | 21.6 | 11.7 | " |
|  | 0.5 | 10.3 | 13.5 | 4.0 | 23.0 | 11.0 | " |

The formulation of the growth regulator of this invention is further illustrated by the following Examples. It should be understood that the active compounds, carriers and the mixing proportions of the formulation of this invention are not limited to the Examples. Incidentially, all parts in the following Examples are by weight.

EXAMPLE 1

| | |
|---|---|
| Compound No. 4 | 50 (parts) |
| Sodium alkylsulfate | 2.5 |
| Polyoxyethylene alkylphenyl ether | 2.5 |
| Clay | 45 |

The components above were mixed uniformly and pulverized to form wettable powder.

EXAMPLE 2

| | |
|---|---|
| Compound No. 1 | 10 (parts) |
| Sodium lignin sulfonate | 1 |
| Bentonite | 30 |
| Talc | 59 |

All the components were mixed uniformly and formed into granules by the use of a granulator.

EXAMPLE 3

| | |
|---|---|
| Compound No. 2 | 10 (parts) |
| Polyoxyethylene alkylphenyl ether | 7 |
| Calcium alkylarylsulfonate | 3 |
| Xylene | 60 |
| Cyclohexanone | 20 |

All the components were thoroughly mixed to form an emulsion.

EXAMPLE 4

| | |
|---|---|
| Compound No. 14 | 50 (parts) |
| Sodium alkylsulfate | 2.5 |
| Polyoxyethylene alkylphenyl ether | 2.5 |
| Clay | 45 |

All the components were mixed uniformly and pulverized to form wettable powder.

EXAMPLE 5

| | |
|---|---|
| Compound No. 17 | 10 (parts) |
| Sodium lignin sulfonate | 1 |
| Bentonite | 30 |
| Talc | 59 |

All the components were mixed uniformly and formed into granules with use of a granulator.

EXAMPLE 6

| | |
|---|---|
| Compound No. 18 | 10 (parts) |
| Polyoxyethylene alkylphenyl ether | 7 |
| Calcium alkylarylsulfonate | 3 |
| Xylene | 60 |
| Cyclohexanone | 20 |

All the components were mixed uniformly to form an emulsion.

What is claimed is:

1. A compound of the formula (I)

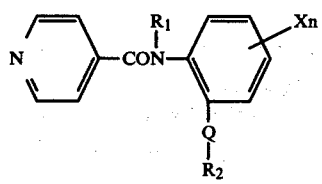

wherein $R_1$ is a hydrogen atom or a $C_1$–$C_4$ alkyl group; X is a halogen atom or methyl; n is an integer of from 0 to 2; $R_2$ is phenyl or halo-substituted phenyl; and Q is

or —$CH_2$—.

2. A compound according to claim 1 of the formula (I) wherein $R_1$, X and n are as defined above; $R_2$ is halo-substituted phenyl; and Q is —CH—.

3. A compound according to claim 1 of the formula (I) wherein $R_1$, X and n are as defined above; $R_2$ is halo-substituted phenyl; and Q is —$CH_2$—.

4. A compound according to claim 1 of the formula (I) wherein $R_1$, X, Q and n are as defined above; and $R_2$ is phenyl.

5. A compound according to claim 1 which is represented by the formula (I) wherein $R_1$, X, Q and n are as defined above and; $R_2$ is mono-halophenyl.

6. A compound according to claim 1 which is represented by the formula (I) wherein $R_1$ is a hydrogen atom; X is 3-chloro; n is 1; Q is $$\begin{array}{c} OH \\ | \\ -CH- \end{array};$$

and $R_2$ is phenyl.

7. A plant growth regulating composition comprising an agriculturally acceptable diluent and as active component an effective amount of one or more compounds of the formula

wherein $R_1$ is a hydrogen atom or a $C_1$–$C_4$ alkyl group; X is a halogen atom or methyl; n is an integer of from 0 to 2; $R_2$ is phenyl or halo-substituted phenyl; and Q is $$\begin{array}{c} OH \\ | \\ -CH- \end{array}$$

or —$CH_2$—.

8. A plant growth regulating composition according to claim 7 the form of which is in wettable powder, emulsion, granule, dust or tablet.

9. A plant growth regulating composition according to claim 7 wherein said composition contains the active component in an amount sufficient to apply to plants in a dose such that the active component can be applied in a dose of from 50 to 100 g/10 ares.

* * * * *

UNITED STATES PATENT AND TRADEMARK OFFICE
CERTIFICATE OF CORRECTION

PATENT NO. : 4,377,407
DATED : March 22, 1983
INVENTOR(S) : Shirakawa et al.

It is certified that error appears in the above–identified patent and that said Letters Patent are hereby corrected as shown below:

Claim 2, line 3 (column 19 of the patent), delete "CH" and insert therefor $\begin{matrix} \text{OH} \\ | \\ \text{--CH--} \end{matrix}$ .

Signed and Sealed this

Eleventh Day of October 1983

[SEAL]

Attest:

Attesting Officer

GERALD J. MOSSINGHOFF

Commissioner of Patents and Trademarks